US011110127B2

(12) United States Patent
Lee

(10) Patent No.: US 11,110,127 B2
(45) Date of Patent: Sep. 7, 2021

(54) USE OF NANOPARTICLES COATED WITH RED BLOOD CELL MEMBRANES TO TREAT HEMOLYTIC DISEASES AND DISORDERS

(71) Applicant: Cellics Therapeutics, Inc., San Diego, CA (US)

(72) Inventor: Tien-Li Lee, Millbrae, CA (US)

(73) Assignee: CELLICS THERAPEUTICS, INC., San Diego, CA (US)

(*) Notice: Subject to any disclaimer, the term of this patent is extended or adjusted under 35 U.S.C. 154(b) by 528 days.

(21) Appl. No.: 15/315,709

(22) PCT Filed: May 29, 2015

(86) PCT No.: PCT/US2015/033366
§ 371 (c)(1),
(2) Date: Dec. 1, 2016

(87) PCT Pub. No.: WO2015/187502
PCT Pub. Date: Dec. 10, 2015

(65) Prior Publication Data
US 2017/0095510 A1    Apr. 6, 2017

Related U.S. Application Data

(60) Provisional application No. 62/006,796, filed on Jun. 2, 2014.

(51) Int. Cl.
*A61K 35/18* (2015.01)
*A61K 9/50* (2006.01)
*A61K 45/00* (2006.01)

(52) U.S. Cl.
CPC ............ *A61K 35/18* (2013.01); *A61K 9/5031* (2013.01); *A61K 9/5068* (2013.01); *A61K 45/05* (2013.01)

(58) Field of Classification Search
None
See application file for complete search history.

(56) References Cited

U.S. PATENT DOCUMENTS

| | | | |
|---|---|---|---|
| 5,358,722 A | 10/1994 | Monzyk | |
| 5,491,219 A | 2/1996 | Mann | |
| 5,653,999 A | 8/1997 | Gaudreault et al. | |
| 6,312,685 B1 | 11/2001 | Fisher et al. | |
| 6,395,029 B1 | 5/2002 | Levy | |
| 8,835,387 B2 | 9/2014 | Chiang et al. | |
| 9,539,210 B2 | 1/2017 | Andrian et al. | |
| 2004/0110695 A1 | 6/2004 | Dobbie | |
| 2004/0180094 A1 | 9/2004 | Joyce | |
| 2006/0292174 A1 | 12/2006 | Rios et al. | |
| 2007/0243137 A1 | 10/2007 | Hainfeld | |
| 2007/0258889 A1 | 11/2007 | Douglas et al. | |
| 2009/0274630 A1 | 11/2009 | Huang | |
| 2010/0055167 A1 | 3/2010 | Zhang et al. | |
| 2013/0028962 A1 | 1/2013 | Zhang et al. | |
| 2013/0337066 A1 | 12/2013 | Zhang et al. | |
| 2016/0136106 A1 | 5/2016 | Zhang et al. | |
| 2017/0000875 A1 | 1/2017 | Hu | |
| 2017/0079909 A1 | 3/2017 | Zhang et al. | |
| 2017/0095510 A1 | 4/2017 | Lee | |
| 2017/0274059 A1 | 9/2017 | Zhang et al. | |
| 2017/0367990 A1 | 12/2017 | Lee | |
| 2018/0085320 A1 | 3/2018 | Zhang et al. | |
| 2018/0140558 A1 | 5/2018 | Zhang et al. | |
| 2018/0153821 A1 | 6/2018 | Zhang et al. | |
| 2018/0169027 A1 | 6/2018 | Zhang et al. | |

FOREIGN PATENT DOCUMENTS

| | | | |
|---|---|---|---|
| WO | 2010014081 A1 | 2/2010 | |
| WO | 2010070620 A1 | 6/2010 | |
| WO | 2011002239 A2 | 1/2011 | |
| WO | WO 2013/052167 | * 4/2013 | ............... A61K 9/51 |
| WO | 2013052167 A2 | 4/2017 | |
| WO | 2017087897 A | 5/2017 | |

OTHER PUBLICATIONS

The website downloaded Mar. 20, 2019: https://rarediseases.info.nih.gov/diseases/6589/hemophagocytic-lymphohistiocytosis#ref_7853 (Year: 2019).*
Janka and Lehmberg, Hematology Am Soc Hematol Educ Program, 2013; 2013: 605-11 (Year: 2013).*
Dhaliwal et al., Am Fam Physician 2004;69:2599-2606 (Year: 2004).*
Joseph A. Trapani and Ilia Voskoboinik, Advances in experimental medicine and biology, 2007; 601: 235-242 (Year: 2007).*
Hall et al., haematologica, 2014; 99: 588-596; doi:10.3324/haemato/.2012.082081 (Year: 2014).*
Dean L. Blood Groups and Red Cell Antigens [Internet]. Bethesda (MD): National Center for Biotechnology Information (US); 2005. Chapter 4, Hemolytic disease of the newborn; 5 pages total (Year: 2005).*
Non-Final Office Action for U.S. Appl. No. 13/827,906, dated Apr. 9, 2019, 21 pages.
Response to Office Action for U.S. Appl. No. 15/505,148, dated Aug. 7, 2019, 14 pages.
Final Office Action for U.S. Appl. No. 15/505,148, dated Aug. 22, 2019, 11 pages.

(Continued)

*Primary Examiner* — Christina M Borgeest
(74) *Attorney, Agent, or Firm* — Rimon, P.C.

(57) ABSTRACT

The present invention relates to methods, combinations and pharmaceutical compositions for treating or preventing a hemolytic disease or condition in a mammal, wherein: said hemolytic disease or condition is caused by an attack of said mammal's red blood cells by said mammal's own body, or said mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother. The exemplary hemolytic diseases or conditions include hemophagocytic lymphohistiocytosis, an autoimmune disease or condition, or a hereditary hemolytic disease or disorder.

16 Claims, No Drawings

(56) References Cited

OTHER PUBLICATIONS

Irhe website downloaded Mar. 20, 2019: https://rarediseases.info.nih.gov/diseases/6589/hemophagocytic-ymphohistiocytosis#ref_7853 (Year: 2019).
Response to Non-Final Office Action for U.S. Appl. No. 13/827,906, dated Oct. 7, 2019, 27 pages.
Office Action for U.S. Appl. No. 13/827,906, dated Nov. 27, 2020, 20 pages.
Amendment and Response to Final Office Action for U.S. Appl. No. 13/827,906, dated Apr. 27, 2021, 53 pages.
Amendment and Response to Final Office Action for U.S. Appl. No. 15/505,148, dated Feb. 18, 2020, 9 pages.
Non-Final Office Action for U.S. Appl. No. 15/505,148, dated Apr. 29, 2020, 11 pages.
Amendment and Response to Non-Final Office Action for U.S. Appl. No. 15/505,148, dated Oct. 27, 2020, 10 pages.
Final Office Action for U.S. Appl. No. 15/505,148, dated Nov. 16, 2020, 5 pages.
Hu et al., "A biomimetic nanosponge that absorbs pore-forming toxins," Nature Nanotechnology vol. 8, May 2013, p. 336-340 https://doi.org/10.1038/nnano.2013.54.
Written Opinion for patent application PCT/US2015/033366, dated Sep. 2, 2015, 7 pages.
International Search Report for patent application PCT/US2015/033366, dated Sep. 2, 2015, 3 pages.
International Preliminary Report on Patentability for patent application PCT/US2015/033366, dated Dec. 6, 2016, 8 pages.
Written Opinion of the International Searching Authority for patent application PCT/US2012/039411, dated Apr. 8, 2013, 4 pages.
International Search Report for patent application PCT/US2012/039411, dated Apr. 8, 2013, 3 pages.
International Preliminary Report for patent application PCT/US2012/039411, dated Mar. 25, 2014, 5 pages.
Written Opinion of the International Searching Authority for patent application PCT/US15/46016, dated Dec. 4, 2015, 7 pages.
International Search Report for patent application PCT/US15/46016, dated Dec. 4, 2015, 3 pages.
International Preliminary Report for patent application PCT/US15/046016, dated Feb. 21, 2017, 8 pages.
U.S., Office Action for U.S. Appl. No. 13/827,906, dated Aug. 20, 2014, 16 pages.
U.S., Response to Office Action for U.S. Appl. No. 13/827,906, dated Feb. 20, 2015, 15 pages.
U.S., Office Action for U.S. Appl. No. 13/827,906, dated Feb. 17, 2016, 20 pages.
U.S., Response to Office Action for U.S. Appl. No. 13/827,906, dated Aug. 15, 2016, 74 pages.
U.S., Office Action for U.S. Appl. No. 13/827,906, dated Feb. 27, 2017, 19 pages.
U.S., Response to office Action for U.S. Appl. No. 13/827,906, dated May 30, 2017, 21 pages.
U.S., Office Action for U.S. Appl. No. 13/827,906, dated Nov. 30, 2017, 14 pages.
U.S., Response to Office Action for U.S Appl. No. 13/827,906, dated May 30, 2018, 14 pages.
U.S., Office Action for U.S. Appl. No. 15/505,148, dated Feb. 7, 2019, 7 pages.
U.S., List of References by examiner for U.S. Appl. No. 15/315,709, dated Dec. 14, 2018, 1 page.
Hu et al. "Marker-of-self functionalization of nanoscale particles through a top-down cellular membrane coating approach," Nanoscale, Apr. 7, 2013, 5(7), p. 2664-2668 https://www.ncbi.nlm.nih.gov/pmc/articles/PMC3667603/.
Hu et al. "Erythrocyte membrane-camouflaged polymeric nanoparticles as a biomimetic delivery platform," Proceedings of the National Academy of Sciences, Jul. 5, 2011. vol. 108. No. 27, p. 10980-10985 www.pnas.org/cgi/doi/10.1073/pnas.1106634108.
Yoo et al. "In vitro and in vivo anti-tumor activities of nanopartides based on doxorubicin—PLGA conjugates," Journal of Controlled Release, Sep. 3, 2000, vol. 68, Issue 3, pp. 419-431 https://doi.org/10.1016/S0168-3659(00)00280-7.
Gao et al. "Modulating Antibacterial Immunity via Bacterial Membrane-Coated Nanoparticles," Nano Lett. 2015, 15, p. 1403-1409 DOI: 10.1021/nl504798g.
Hu et al. "Nanopartide biointerfacing by platelet membrane cloaking," Nature, vol. 526, p. 118, Oct. 1, 2015 d oi: 10.1038/nature15373.
Fang et al. "Cancer Cell Membrane-Coated Nanoparticles for Anticancer Vaccination and Drug Delivery," Nano Lett. 2014, 14, 2181-2188, dx.doi.org/10.1021/nl500618u.
Some Definitions of Constituent by Merriam-Webster, http://www.merriam-webster.com/dictionary/constituent, Aug. 15, 2016.

* cited by examiner

USE OF NANOPARTICLES COATED WITH RED BLOOD CELL MEMBRANES TO TREAT HEMOLYTIC DISEASES AND DISORDERS

I. CROSS REFERENCES TO RELATED APPLICATION

This application is the national phase of PCT application PCT/US2015/033366 having an international filing date of May 29, 2015, which claims priority to U.S. Provisional Patent Application No. 62/006,796, filed Jun. 2, 2014. The contents of the above-referenced applications are incorporated by reference herein in their entireties for all purposes.

II. FIELD OF THE INVENTION

The present invention relates to methods, combinations and pharmaceutical compositions for treating or preventing a hemolytic disease or condition in a mammal, wherein: said hemolytic disease or condition is caused by an attack of said mammal's red blood cells by said mammal's own body, or said mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother. The exemplary hemolytic diseases or conditions include hemophagocytic lymphohistiocytosis, an autoimmune disease or condition, or a hereditary hemolytic disease or disorder.

III. BACKGROUND OF THE INVENTION

Hemophagocytic Lymphohistiocytosis (HLH—also called Erythrophagocytic Lymphohistiocytosis) is a disease uniformly fatal if not treated (a published review reports <10% survival after 3 years) and has an annual incidence of about 1.2 cases per million persons. See Arico M., Janka G., Fischer A., et al. *Hemophagocytic lymphohistiocytosis. Report of* 122 *Children From the International Registry*; and Feldmann J, Le Deist F, Ouachee-Chardin M, et al., Functional consequences of perforin gene mutations in 22 patients with familial haemophagocytic lymphohistiocytosis. Br J Haematol. June 2002; 117(4):965-72. FHL Study Group of the Histiocyte Society. Leukemia. February 1996; 10(2):197-203. HLH has several forms, but is often hereditary (autosomal recessive) and typically manifests in infancy. The most common subtype relates to a defective gene for perforin, a pore forming component that lyses red blood cells and is closely related in structure and function to complement component 9 (C9). The course of disease often includes waxing and waning signs and symptoms with episodes of acute exacerbations and hemolysis. Current treatments are unsatisfactory and involve the use of cytotoxic compounds, immunosuppressants, or IVIG with marginal efficacy.

There are other diseases or conditions that have hemolytic crises as a hallmark of illness. Exemplary clinical indications include glucose-6-phosphate dehydrogenase deficiency, sickle cell disease, and several others. For these diseases or conditions, patients generally have manageable disease except during acute episodes of hemolysis.

Therefore, what are needed are improved treatments and/or prevention of the various hemolytic diseases or conditions. The present invention addresses these and other related needs in the art.

IV. SUMMARY OF THE INVENTION

In one aspect, the present invention provides for a method for treating or preventing a hemolytic disease or condition in a mammal, which method comprises administering, to a mammal in need of treatment or prevention of a hemolytic disease or condition, an effective amount of a nanoparticle comprising a) an inner core comprising a non-cellular material, and b) an outer surface comprising a cellular membrane derived from a red blood cell, wherein: said hemolytic disease or condition is caused by an attack of said mammal's red blood cells by said mammal's own body, or said mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother.

In another aspect, the present invention is directed to an use of an effective amount of a nanoparticle for the manufacture of a medicament for treating or preventing a hemolytic disease or condition in a mammal, wherein said hemolytic disease or condition is caused by an attack of said mammal's red blood cells by said mammal's own body, or said mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother and said nanoparticle comprising a) an inner core comprising a non-cellular material, and b) an outer surface comprising a cellular membrane derived from a red blood cell.

In still another aspect, the present invention provides for a combination for treating and/or preventing a hemolytic disease or condition in a mammal, which combination comprises an effective amount of a nanoparticle and an effective amount of a second prophylactic or therapeutic agent for treating and/or preventing a hemolytic disease or condition in a mammal, wherein said hemolytic disease or condition is caused by an attack of said mammal's red blood cells by said mammal's own body, or said mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother and said nanoparticle comprising a) an inner core comprising a non-cellular material, and b) an outer surface comprising a cellular membrane derived from a red blood cell. The present invention also provides for a pharmaceutical composition comprising the combination and a method for treating and/or preventing a hemolytic disease or condition in a mammal using the combination or the pharmaceutical composition comprising the combination.

Exemplary hemolytic diseases or conditions include hemophagocytic lymphohistiocytosis, an autoimmune disease or condition, e.g., autoimmune hemolytic anemia, or a hereditary hemolytic disease or disorder, e.g., familial hemophagocytic lymphohistiocytosis (FHL), glucose-6-phosphate dehydrogenase deficiency, and sickle cell disease. In some embodiments, the mammal to be treated is a pregnant mammal and the hemolytic disease or condition of a fetus of the pregnant mammal is caused by an attack of the fetus' red blood cells by an antibody of the pregnant mammal.

In some aspects, the prevent disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

V. DETAILED DESCRIPTION OF THE INVENTION

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual*, 2$^{nd}$ ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy*, 20$^{th}$ ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (PIP3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Methods for Treating or Preventing a Hemolytic Disease or Condition in a Mammal In one aspect, the present invention provides for a method for treating or preventing a hemolytic disease or condition in a mammal, which method comprises administering, to a mammal in need of treatment or prevention of a hemolytic disease or condition, an effective amount of a nanoparticle comprising a) an inner core comprising a non-cellular material, and b) an outer surface comprising a cellular membrane derived from a red blood cell, wherein: said hemolytic disease or condition is caused by an attack of said mammal's red blood cells by said mammal's own body, or said mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother.

The present methods can be used to treat or prevent a hemolytic disease or condition in any suitable mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the present methods can be used for treating a hemolytic disease or condition. In other embodiments, the present methods can be used for preventing a hemolytic disease or condition.

The present methods can be used for treating or preventing any suitable hemolytic disease or condition in a mammal, wherein the hemolytic disease or condition is caused by an attack of said mammal's red blood cells by said mammal's own body, or the mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother. Exemplary hemolytic diseases or conditions include hemophagocytic lymphohistiocytosis and an autoimmune disease or condition.

The present methods can be used for treating or preventing any suitable forms of hemophagocytic lymphohistiocytosis. In some embodiments, the hemophagocytic lymphohistiocytosis is primary hemophagocytic lymphohistiocytosis (FHL). The FHL can be of any suitable genetic subtype, such as FHL1, FHL2, FHL3, FHL4, and FHL5. The FHL1 can be associated with a defect in HPLH1 (hemophagocytic lymphohistiocytosis 1). The FHL2 can be associated with a defect in PRF1 (Perforin). The FHL3 can be associated with a defect in UNC13D (Munc13-4). The FHL4 can be associated with a defect in STX11 (Syntaxin 11). The FHL5 can be associated with a defect in STXBP2 (Syntaxin binding protein 2)/UNC18-2. In other embodiments, the hemophagocytic lymphohistiocytosis is secondary haemophagocytic lymphohistiocytosis (acquired haemophagocytic lymphohistiocytosis), such as the secondary haemophagocytic lymphohistiocytosis that can occur with systemic infection, immunodeficiency, or underlying malignancy.

The present methods can be used for treating or preventing any suitable forms of a hemolytic disease or condition that is an autoimmune disease or condition, e.g., autoimmune hemolytic anemia. In some embodiments, the autoimmune disease or condition is warm antibody autoimmune hemolytic anemia (WAIHA). The WAIHA can be caused by an IgG or an IgA antibody. The WAIHA can also be caused by an abnormal hapten on the red blood cell membrane of the mammal. For example, certain drugs, especially penicillin and cephalosporins, can bind to certain proteins on the red blood cell membrane and act as abnormal haptens. The WAIHA can also be caused by an autoantibody. For example, certain drugs can cause antibodies to be made against mammal's own red blood cells and lead to the destruction of mammal's own red blood cells. Typically, the WAHA occurs at temperatures of 37 degrees centigrade or higher.

In other embodiments, the autoimmune disease or condition is cold antibody hemolytic anemia (CAHA). The CAHA can be a primary CAHA or a secondary CAHA. The secondary CAHA can be associated with an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus). Typically, the CAHA occurs at temperatures of approximately 0 to 10 degrees centigrade.

In some embodiments, the mammal is a pregnant mammal and the hemolytic disease or condition of a fetus of the pregnant mammal is caused by an attack of the fetus' red blood cells by an antibody of the pregnant mammal. The present methods can be used for treating or preventing the hemolytic disease or condition of a fetus of the pregnant mammal caused by an attack of the fetus' red blood cells by a variety of antibodies of the pregnant mammal, e.g., an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof. In some embodiments, the mammal is a baby and the hemolytic disease or condition of the baby is caused by an attack of the baby's red blood cells by an antibody of the baby's mother. The present methods can be used for treating or preventing the hemolytic disease or condition of a baby caused by an attack of the baby's red blood cells by a variety of antibodies of the baby's mother, e.g., an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof.

In some embodiments, the hemolytic disease or condition is a hereditary hemolytic disease or disorder. The present methods can be used for treating or preventing a variety of hereditary hemolytic diseases or disorders, e.g., FHL, glucose-6-phosphate dehydrogenase deficiency, and sickle cell disease. In some embodiments, the hereditary hemolytic disease or disorder is glucose-6-phosphate dehydrogenase deficiency. The present methods can be used for treating or preventing any suitable forms of glucose-6-phosphate dehydrogenase deficiency, e.g., a genetic subtype G6PD A or G6PD Mediterranean. In other embodiments, the hereditary hemolytic disease or disorder is sickle cell disease.

The present methods can use any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, e.g., a plasma membrane derived from a human red blood cell. In some embodiments, The nanoparticle can comprise any suitable naturally occurring cellular membrane derived from a red blood cell. In some embodiments, the cellular membrane comprises a naturally occurring plasma membrane derived from a red blood cell, e.g., a naturally occurring plasma membrane derived from a human red blood cell.

The present methods can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, or a combination thereof. In another example, the releasable cargo can be a metallic particle, a polymeric particle, a dendrimer particle, or an inorganic particle.

The nanoparticle can have any suitable size. For example, the nanoparticle can have a diameter from about 10 nm to about 10 µm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the red blood cell from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the red blood cell from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the mammal's or fetus' red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the mammal's or fetus' red blood cells.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the outer surface of the nanoparticle can further comprise a synthetic membrane.

In some embodiments, the nanoparticle substantially lacks immunogenicity to the mammal. For example, the cellular membrane can be derived from a red blood cell from the same species of the mammal. In another example, the mammal is a human and the cellular membrane is derived from a human red blood cell. In some embodiments, the cellular membrane can be derived from a red blood cell of the mammal to be treated. For example, the cellular membrane can be derived from a red blood cell of the human to be treated.

In some embodiments, the present methods can further comprise administering another active ingredient to the mammal. The other active ingredient can be used to treat, prevent or manage the hemolytic disease or condition in the mammal. For example, if the hemolytic disease or condition to be treated and/or prevented is hemophagocytic lymphohistiocytosis, the present methods can further comprise administering corticosteroids, e.g., high dose corticosteroids, etoposide, cyclosporin, intravenous immunoglobulin, methotrexate and/or vincristine. In another example, if the hemolytic disease or condition to be treated and/or prevented is warm antibody autoimmune hemolytic anemia, the present methods can further comprise administering corticosteroids, immunoglobulins, e.g., high dose intravenous immune globulin, prednisone, rituximab, danazol, cyclosphosphamide, azathioprine, and/or cyclosporine. In still another example, if the hemolytic disease or condition to be treated and/or prevented is cold antibody hemolytic anemia, the present methods can further comprise administering intravenous immunoglobulin (IVIG) or therapeutic agents for treating underlying condition, e.g., malignancy such as lymphoma. If cold antibody hemolytic anemia is a secondary CAHA, e.g., CAHA associated with an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus), the present methods can further comprise administering therapeutic agents for treating and/or managing the underlying cause of the secondary CAHA, e.g., therapeutic agents for treating and/or managing an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus).

In some embodiments, the hemolytic disease or condition to be treated and/or prevented is the hemolytic disease or condition of a fetus of the pregnant mammal that is caused by an attack of the fetus' red blood cells by an antibody of the pregnant mammal. The present methods can further comprise administering therapeutic agents for blocking and/or minimizing the attack of the fetus' red blood cells by an antibody of the pregnant mammal. For example, the additional therapeutic agents can be used to block and/or minimize the attack of the fetus' red blood cells by an antibody of the pregnant mammal, e.g., an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof.

In some embodiments, the hemolytic disease or condition to be treated and/or prevented is a hereditary hemolytic disease or disorder. The present methods can further comprise administering therapeutic agents for treating and/or managing the hereditary hemolytic disease or disorder. For example, if hereditary hemolytic disease or disorder is glucose-6-phosphate dehydrogenase deficiency, the present methods can further comprise administering folic acid. In another example, if hereditary hemolytic disease or disorder is sickle cell disease, the present methods can further comprise administering folic acid, penicillin, anti-malarial chemoprophylaxis, an analgesic, opioid, nonsteroidal anti-inflammatory drugs (NSAID), an antibiotics, e.g., quinolone or macrolide, and/or hydroxyurea.

In some embodiments, the present methods can further comprise administering a pharmaceutically acceptable carrier or excipient to the mammal.

The nanoparticle can be administered using any suitable delivery mechanisms or techniques. In some embodiments, the nanoparticle can be administered alone. In other embodiments, the nanoparticle can be administered with a pharmaceutically acceptable carrier or excipient. In still other embodiments, the nanoparticle can be administered via a medicament delivery system.

The present methods can further comprise assessing efficacy of nanoparticle and/or another active ingredient in treating or preventing the hemolytic disease or condition in the mammal. The efficacy of nanoparticle and/or another active ingredient in treating or preventing the hemolytic disease or condition can be assessed using any suitable tests. For example, the efficacy of nanoparticle and/or another active ingredient can be assessed by complete blood cell count (CBC) with differential count, serum lactate dehydrogenase (LDH) test, peripheral blood smear test, serum haptoglobin test, indirect bilirubin test, urine free hemoglobin test, urine hemosiderin test, and red blood cell survival (chromium Cr 51 [51 Cr] survival) test. The above tests can have utility in tracking progress or efficacy of a treatment, especially, but not exclusively via serial measurement. Many of these tests are not absolutely specific to hemolysis and there can be false positives in most of these tests (but unlikely to be false negatives).

Low mean corpuscular volume (MCV) and mean corpuscular hemoglobin (MCH) are seen with chronic intravascular hemolysis. Red blood cell distribution width (RDW) increases occur in hemolytic anemias. An increased reticulocyte count represents increased RBC production and is associated with hemolysis (although other conditions can cause its increase too). In some embodiments, recovery to more normal measurements in one or more of the above tests relates to an effective treatment. Although there are confounding factors and theoretically false positives with MCV, MCH, RDW, and reticulocyte count, as a variety of conditions can affect those measures. But from a practical standpoint, surveillance of these laboratory parameters, especially when used in combination, often can be used to assess the efficacy of the treatment.

Serum LDH elevation can be very sensitive for hemolysis, but is not specific, as LDH is ubiquitous and can be released from other damaged cells as well. LDH isozymes 1 and 2 are more specific for RBC destruction, but these are also increased in myocardial infarction. Peripheral blood smear, i.e., microscopic evaluation of blood cells, can also be used to assess the mechanism and extent of hemolysis. A low serum haptoglobin is a criterion for moderate-to-severe hemolysis. A decrease in serum haptoglobin is often more likely in intravascular hemolysis than in extravascular hemolysis. But as an acute phase reactant, haptoglobin levels can be normal or elevated despite significant hemolysis in patients with infections and in other reactive states. Unconjugated bilirubin is a criterion for hemolysis, but it is not specific. Red blood cell survival (chromium Cr 51 [51 Cr] survival) can be used to demonstrate shortened red blood cell survival due to hemolysis. Other exemplary tests include urine free hemoglobin test and urine hemosiderin test. In some embodiments, recovery to more normal measurements in one or more of the above tests relates to an effective treatment.

In some embodiments, the efficacy of nanoparticle can be assessed by at least two of the tests, e.g., 2, 3, 4, 5, 6, 7, 8 or 9 of the above tests.

In some embodiments, the efficacy of nanoparticle and/or another active ingredient in treating or preventing the autoimmune hemolytic anemia is assessed. The efficacy of nanoparticle in treating or preventing the autoimmune hemolytic anemia can be assessed using any suitable tests. For example, the efficacy of nanoparticle and/or another active ingredient in treating or preventing the autoimmune hemolytic anemia can be assessed using the direct antiglobulin test (DAT), the polybrene test and/or the immunoradiometric assay (IRMA) to detects red blood cell-bound IgG.

The Direct antiglobulin test (DAT) is useful to detect autoimmune hemolytic anemia (AIHA), but can have a false negative too. However, the polybrene test can detect DAT-negative AIHA. (See e.g., Garratty G Immune hemolytic anemia associated with negative routine serology. Semin Hematol. July 2005; 42(3):156-64.) The immunoradiometric assay (IRMA) can also be used to diagnose AIHA in DAT negative patients because IRMA can be used to detect red blood cell-bound IgG. (See e.g., Kamesaki T, Oyamada T, Omine M, Ozawa K, Kajii E. Cut-off value of red-blood-cell-bound IgG for the diagnosis of Coombs-negative autoimmune hemolytic anemia. Am J Hematol. February 2009; 84(2):98-101.)

In one exemplary embodiment, serum can be obtained from a patient confirmed to have autoimmune hemolytic anemia and are separated into different samples. One sample can be untreated, and another can be incubated with a measured quantity of the nanoparticles. A subsequent DAT, polybrene, or IRMA test can be used to measure whether the nanoparticles have positive effect. Depending on the on/off rate of the antibodies used in the tests, test time or incubation conditions can be designed to yield a positive result that correlates with clinical effect of the nanoparticles.

The nanoparticle, alone or in combination with other active ingredient(s), can be administered via any suitable administration routes. In some embodiments, the nanoparticle, alone or in combination with other active ingredient(s), can be administered via oral, parenteral, rectal, nasal, topical, or ocular routes, or by inhalation. Exemplary parenteral administration routes include intravenous, intramuscular, intraperitoneal, intranasal, and subcutaneous routes.

C. Use of an Effective Amount of a Nanoparticle for the Manufacture of a Medicament for Treating or Preventing a Hemolytic Disease or Condition in a Mammal In another aspect, the present invention is directed to an use of an effective amount of a nanoparticle for the manufacture of a medicament for treating or preventing a hemolytic disease or condition in a mammal, wherein said hemolytic disease or condition is caused by an attack of said mammal's red blood cells by said mammal's own body, or said mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother and said nanoparticle comprising a) an inner core comprising a non-cellular material, and b) an outer surface comprising a cellular membrane derived from a red blood cell.

The manufactured medicament can be used to treat or prevent a hemolytic disease or condition in any suitable mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the manufactured medicament can be used for treating a hemolytic disease or condition. In other embodiments, the manufactured medicament can be used for preventing a hemolytic disease or condition.

The manufactured medicament can be used for treating or preventing any suitable hemolytic disease or condition in a mammal, wherein the hemolytic disease or condition is caused by an attack of said mammal's red blood cells by said mammal's own body, or the mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother. Exemplary hemolytic diseases or conditions include hemophagocytic lymphohistiocytosis and an autoimmune disease or condition.

The manufactured medicament can be used for treating or preventing any suitable forms of hemophagocytic lymphohistiocytosis. In some embodiments, the hemophagocytic lymphohistiocytosis is primary hemophagocytic lymphohistiocytosis (FHL). The FHL can be of any suitable genetic subtype, such as FHL1, FHL2, FHL3, FHL4, and FHL5. The FHL1 can be associated with a defect in HPLH1 (hemophagocytic lymphohistiocytosis 1). The FHL2 can be associated with a defect in PRF1 (Perforin). The FHL3 can be associated with a defect in UNC13D (Munc13-4). The FHL4 can be associated with a defect in STX11 (Syntaxin 11). The FHL5 can be associated with a defect in STXBP2 (Syntaxin binding protein 2)/UNC18-2. In other embodiments, the hemophagocytic lymphohistiocytosis is secondary haemophagocytic lymphohistiocytosis (acquired haemophagocytic lymphohistiocytosis), such as the secondary haemophagocytic lymphohistiocytosis that can occur with systemic infection, immunodeficiency, or underlying malignancy.

The manufactured medicament can be used for treating or preventing any suitable forms of a hemolytic disease or condition that is an autoimmune disease or condition, e.g., autoimmune hemolytic anemia. In some embodiments, the autoimmune disease or condition is warm antibody autoimmune hemolytic anemia (WAIHA). The WAIHA can be caused by an IgG or an IgA antibody. The WAIHA can also be caused by an abnormal hapten on the red blood cell membrane of the mammal. For example, certain drugs, especially penicillin and cephalosporins, can bind to certain proteins on the red blood cell membrane and act as abnormal haptens. The WAIHA can also be caused by an autoantibody. For example, certain drugs can cause antibodies to be made against mammal's own red blood cells and lead to the destruction of mammal's own red blood cells. Typically, the WAHA occurs at temperatures of 37 degrees centigrade or higher.

In other embodiments, the autoimmune disease or condition is cold antibody hemolytic anemia (CAHA). The CAHA can be a primary CAHA or a secondary CAHA. The method secondary CAHA can be associated with an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus). Typically, the CAHA occurs at temperatures of approximately 0 to 10 degrees centigrade.

In some embodiments, the mammal is a pregnant mammal and the hemolytic disease or condition of a fetus of the pregnant mammal is caused by an attack of the fetus' red blood cells by an antibody of the pregnant mammal. The manufactured medicament can be used for treating or preventing the hemolytic disease or condition of a fetus of the pregnant mammal caused by an attack of the fetus' red blood cells by a variety of antibodies of the pregnant mammal, e.g., an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof. In some embodiments, the mammal is a baby and the hemolytic disease or condition of the baby is caused by an attack of the baby's red blood cells by an antibody of the baby's mother. The manufactured medicament can be used for treating or preventing the hemolytic disease or condition of a baby caused by an attack of the baby's red blood cells by a variety of antibodies of the baby's mother, e.g., an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof.

In some embodiments, the hemolytic disease or condition is a hereditary hemolytic disease or disorder. The manufactured medicament can be used for treating or preventing a variety of hereditary hemolytic diseases or disorders, e.g., FHL, glucose-6-phosphate dehydrogenase deficiency, and sickle cell disease. In some embodiments, the hereditary hemolytic disease or disorder is glucose-6-phosphate dehydrogenase deficiency. The manufactured medicament can be used for treating or preventing any suitable forms of glucose-6-phosphate dehydrogenase deficiency, e.g., a genetic subtype G6PD A or G6PD Mediterranean. In other embodiments, the hereditary hemolytic disease or disorder is sickle cell disease.

The manufactured medicament can use any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, e.g., a plasma membrane derived from a human red blood cell. In some embodiments, The nanoparticle can comprise any suitable naturally occurring cellular membrane derived from a red blood cell. In some embodiments, the cellular membrane comprises a naturally occurring plasma membrane derived from a red blood cell, e.g., a naturally occurring plasma membrane derived from a human red blood cell.

The manufactured medicament can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, or a combination thereof. In another example, the releasable cargo can be a metallic particle, a polymeric particle, a dendrimer particle, or an inorganic particle.

The nanoparticle can have any suitable size. For example, the nanoparticle can have a diameter from about 10 nm to about 10 μm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the red blood cell from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the red blood cell from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the mammal's or fetus' red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the mammal's or fetus' red blood cells.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the outer surface of the nanoparticle can further comprise a synthetic membrane.

In some embodiments, the nanoparticle substantially lacks immunogenicity to the mammal. For example, the cellular membrane can be derived from a red blood cell from the same species of the mammal. In another example, the mammal is a human and the cellular membrane is derived from a human red blood cell. In some embodiments, the cellular membrane can be derived from a red blood cell of the mammal to be treated. For example, the cellular membrane can be derived from a red blood cell of the human to be treated.

In some embodiments, the manufactured medicament can further comprise another active ingredient to the mammal. The other active ingredient can be used to treat or prevent the hemolytic disease or condition in the mammal. For example, if the hemolytic disease or condition to be treated and/or prevented is hemophagocytic lymphohistiocytosis, the manufactured medicament can further comprise corticosteroids, e.g., high dose corticosteroids, etoposide, cyclosporin, intravenous immunoglobulin, methotrexate and/or vincristine. In another example, if the hemolytic disease or condition to be treated and/or prevented is warm antibody autoimmune hemolytic anemia, the manufactured medicament can further comprise corticosteroids, immunoglobulins, e.g., high dose intravenous immune globulin, prednisone, rituximab, danazol, cyclosphosphamide, azathioprine, and/or cyclosporine. In still another example, if the hemolytic disease or condition to be treated and/or prevented is cold antibody hemolytic anemia, the manufactured medicament can further comprise intravenous immunoglobulin (IVIG) or therapeutic agents for treating underlying condition, e.g., malignancy such as lymphoma. If cold antibody hemolytic anemia is a secondary CAHA, e.g., CAHA associated with an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus), the manufactured medicament can further comprise therapeutic agents for treating and/or managing the underlying cause of the secondary CAHA, e.g., therapeutic agents for treating and/or managing an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus).

In some embodiments, the hemolytic disease or condition to be treated and/or prevented is the hemolytic disease or condition of a fetus of the pregnant mammal that is caused by an attack of the fetus' red blood cells by an antibody of the pregnant mammal. The manufactured medicament can further comprise therapeutic agents for blocking and/or minimizing the attack of the fetus' red blood cells by an antibody of the pregnant mammal. For example, the additional therapeutic agents can be used to block and/or minimize the attack of the fetus' red blood cells by an antibody of the pregnant mammal, e.g., an anti-A antibody, an anti-B antibody, an anti-rhesus C antibody, an anti-e antibody, an anti-Kell antibody, an anti-Lewis antibody, an anti-Duffy antibody, an anti-P antibody, or an anti-MN antibody.

In some embodiments, the hemolytic disease or condition to be treated and/or prevented is a hereditary hemolytic disease or disorder. The manufactured medicament can further comprise therapeutic agents for treating and/or managing the hereditary hemolytic disease or disorder. For example, if hereditary hemolytic disease or disorder is glucose-6-phosphate dehydrogenase deficiency, the manufactured medicament can further comprise folic acid. In another example, if hereditary hemolytic disease or disorder is sickle cell disease, the manufactured medicament can further comprise folic acid, penicillin, anti-malarial chemoprophylaxis, an analgesic, opioid, nonsteroidal anti-inflammatory drugs (NSAID), an antibiotics, e.g., quinolone or macrolide, and/or hydroxyurea.

In some embodiments, the manufactured medicament can further comprise a pharmaceutically acceptable carrier or excipient to the mammal.

The manufactured medicament can be administered using any suitable delivery mechanisms or techniques. In some embodiments, the nanoparticle in the manufactured medicament can be administered alone. In other embodiments, the nanoparticle in the manufactured medicament can be administered with a pharmaceutically acceptable carrier or excipient. In still other embodiments, the nanoparticle in the manufactured medicament can be administered via a medicament delivery system.

The manufactured medicament, alone or in combination with other active ingredient(s), can be administered via any suitable administration routes. In some embodiments, the manufactured medicament, alone or in combination with other active ingredient(s), can be administered via oral, parenteral, rectal, nasal, topical, or ocular routes, or by inhalation. Exemplary parenteral administration routes include intravenous, intramuscular, intraperitoneal, intranasal, and subcutaneous routes.

D. Combinations for Treating or Preventing a Hemolytic Disease or Condition in a Mammal and Uses Thereof In still another aspect, the present invention provides for a combination for treating and/or preventing a hemolytic disease or condition in a mammal, which combination comprises an effective amount of a nanoparticle and an effective amount of a second prophylactic or therapeutic agent for treating and/or preventing a hemolytic disease or condition in a mammal, wherein said hemolytic disease or condition is caused by an attack of said mammal's red blood cells by said mammal's own body, or said mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother, and said nanoparticle comprising a) an inner core comprising a non-cellular material, and b) an outer surface comprising a cellular membrane derived from a red blood cell.

The present combination can be made, stored and/or used in any suitable formulation. In some embodiments, the present invention provides for a pharmaceutical composition comprising the above combination admixed with at least one pharmaceutically acceptable carrier or excipient. In other embodiments, the present invention provides for a method for treating or preventing a hemolytic disease or condition in a mammal, which method comprises administering, to a mammal in need of treatment or prevention of a hemolytic disease or condition, an effective amount of the above combination or pharmaceutical composition.

The above combination or pharmaceutical composition can be used to treat or prevent a hemolytic disease or condition in any suitable mammal. In some embodiments, the mammal is a human. In other embodiments, the mammal is a non-human mammal, including a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

In some embodiments, the above combination or pharmaceutical composition can be used for treating a hemolytic disease or condition. In other embodiments, the manufactured medicament can be used for preventing a hemolytic disease or condition.

The above combination or pharmaceutical composition can be used for treating or preventing any suitable hemolytic disease or condition in a mammal, wherein the hemolytic disease or condition is caused by an attack of said mammal's red blood cells by said mammal's own body, or the mammal is a pregnant mammal and said hemolytic disease or condition of a fetus of said pregnant mammal is caused by an attack of said fetus' red blood cells by an antibody of said pregnant mammal, or said mammal is a baby and said hemolytic disease or condition of said baby is caused by an attack of said baby's red blood cells by an antibody of said baby's mother. Exemplary hemolytic diseases or conditions include hemophagocytic lymphohistiocytosis and an autoimmune disease or condition.

The above combination or pharmaceutical composition can be used for treating or preventing any suitable forms of hemophagocytic lymphohistiocytosis. In some embodiments, the hemophagocytic lymphohistiocytosis is primary hemophagocytic lymphohistiocytosis (FHL). The FHL can be of any suitable genetic subtype, such as FHL1, FHL2, FHL3, FHL4, and FHL5. The FHL1 can be associated with a defect in HPLH1 (hemophagocytic lymphohistiocytosis 1). The FHL2 can be associated with a defect in PRF1 (Perforin). The FHL3 can be associated with a defect in UNC13D (Munc13-4). The FHL4 can be associated with a defect in STX11 (Syntaxin 11). The FHL5 can be associated with a defect in STXBP2 (Syntaxin binding protein 2)/UNC18-2. In other embodiments, the hemophagocytic lymphohistiocytosis is secondary haemophagocytic lymphohistiocytosis (acquired haemophagocytic lymphohistiocytosis), such as the secondary haemophagocytic lymphohistiocytosis that can occur with systemic infection, immunodeficiency, or underlying malignancy.

The above combination or pharmaceutical composition can be used for treating or preventing any suitable forms of a hemolytic disease or condition that is an autoimmune disease or condition, e.g., autoimmune hemolytic anemia. In some embodiments, the autoimmune disease or condition is warm antibody autoimmune hemolytic anemia (WAIHA). The WAIHA can be caused by an IgG or an IgA antibody. The WAIHA can also be caused by an abnormal hapten on the red blood cell membrane of the mammal. For example, certain drugs, especially penicillin and cephalosporins, can bind to certain proteins on the red blood cell membrane and act as abnormal haptens. The WAIHA can also be caused by an autoantibody. For example, certain drugs can cause antibodies to be made against mammal's own red blood cells and lead to the destruction of mammal's own red blood cells. Typically, the WAHA occurs at temperatures of 37 degrees centigrade or higher.

In other embodiments, the autoimmune disease or condition is cold antibody hemolytic anemia (CAHA). The CAHA can be a primary CAHA or a secondary CAHA. The secondary CAHA can be associated with an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus). Typically, the CAHA occurs at temperatures of approximately 0 to 10 degrees centigrade.

In some embodiments, the mammal is a pregnant mammal and the hemolytic disease or condition of a fetus of the pregnant mammal is caused by an attack of the fetus' red blood cells by an antibody of the pregnant mammal. The above combination or pharmaceutical composition can be used for treating or preventing the hemolytic disease or condition of a fetus of the pregnant mammal caused by an attack of the fetus' red blood cells by a variety of antibodies of the pregnant mammal, e.g., an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof. In some embodiments, the mammal is a baby and the hemolytic disease or condition of the baby is caused by an attack of the baby's red blood cells by an antibody of the baby's mother. The above combination or pharmaceutical composition can be used for treating or preventing the hemolytic disease or condition of a baby caused by an attack of the baby's red blood cells by a variety of antibodies of the baby's mother, e.g., an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof.

In some embodiments, the hemolytic disease or condition is a hereditary hemolytic disease or disorder. The above combination or pharmaceutical composition can be used for treating or preventing a variety of hereditary hemolytic diseases or disorders, e.g., FHL, glucose-6-phosphate dehydrogenase deficiency, and sickle cell disease. In some embodiments, the hereditary hemolytic disease or disorder is glucose-6-phosphate dehydrogenase deficiency. The above combination or pharmaceutical composition can be used for treating or preventing any suitable forms of glucose-6-phosphate dehydrogenase deficiency, e.g., a genetic subtype G6PD A or G6PD Mediterranean. In other embodiments, the hereditary hemolytic disease or disorder is sickle cell disease.

The above combination or pharmaceutical composition can use any suitable nanoparticle. In some embodiments, the inner core of the nanoparticle can comprise a biocompatible or a synthetic material, such as poly(lactic-c-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. The nanoparticle can comprise any suitable cellular membrane derived from a red blood cell. For example, the nanoparticle can comprise a plasma membrane or an intracellular membrane derived from a red blood cell. In some embodiments, the cellular membrane comprises a plasma membrane derived from a red blood cell, e.g., a plasma membrane derived from a human red blood cell. In some embodiments, The nanoparticle can comprise any suitable naturally occurring cellular membrane derived from a red blood cell. In some embodiments, the cellular membrane comprises a naturally occurring plasma membrane derived from a red blood cell, e.g., a naturally occurring plasma membrane derived from a human red blood cell.

The above combination or pharmaceutical composition can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, or a combination thereof. In another example, the releasable cargo can be a metallic particle, a polymeric particle, a dendrimer particle, or an inorganic particle.

The nanoparticle can have any suitable size. For example, the nanoparticle can have a diameter from about 10 nm to about 10 µm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the red blood cell from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the red blood cell from which the cellular membrane is derived. In some embodiments, the nanoparticle comprises a plasma membrane derived from a red blood cell and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane so that the nanoparticle functions as decoy for the mammal's or fetus' red blood cells. For example, the nanoparticle can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the mammal's or fetus' red blood cells.

In some embodiments, the nanoparticle is biocompatible or biodegradable. For example, the inner core of the nanoparticle comprises PLGA and the outer surface of the nanoparticle comprises a plasma membrane derived from a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the outer surface of the nanoparticle can further comprise a synthetic membrane.

In some embodiments, the nanoparticle substantially lacks immunogenicity to the mammal. For example, the cellular membrane can be derived from a red blood cell from the same species of the mammal. In another example, the mammal is a human and the cellular membrane is derived from a human red blood cell. In some embodiments, the cellular membrane can be derived from a red blood cell of the mammal to be treated. For example, the cellular membrane can be derived from a red blood cell of the human to be treated.

In addition to the nanoparticle, the above combination or pharmaceutical composition can comprise any suitable second active ingredient to the mammal, usually depending on the types of the hemolytic disease or condition to be treated and/or prevented. For example, if the hemolytic disease or condition to be treated and/or prevented is hemophagocytic lymphohistiocytosis, the combination or pharmaceutical composition can further comprise corticosteroids, e.g., high dose corticosteroids, etoposide, cyclosporin, intravenous immunoglobulin, methotrexate and/or vincristine. In another example, if the hemolytic disease or condition to be treated and/or prevented is warm antibody autoimmune hemolytic anemia, the combination or pharmaceutical composition can further comprise corticosteroids, immunoglobulins, e.g., high dose intravenous immune globulin, prednisone, rituximab, danazol, cyclophosphamide, azathioprine, and/or cyclosporine. In still another example, if the hemolytic disease or condition to be treated and/or prevented is cold antibody hemolytic anemia, the combination or pharmaceutical composition can further comprise intravenous immunoglobulin (IVIG) or therapeutic agents for treating underlying condition, e.g., malignancy such as lymphoma. If cold antibody hemolytic anemia is a secondary CAHA, e.g., CAHA associated with an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus), the combination or pharmaceutical composition can further comprise therapeutic agents for treating and/or managing the underlying cause of the secondary CAHA, e.g., therapeutic agents for treating and/or managing an infectious disease (e.g., mycoplasma infection, mumps, cytomegalovirus, infectious mononucleosis), an immunoproliferative disease (e.g., non-Hodgkin's lymphoma, chronic lymphocytic leukemia), or a connective tissue disorder (e.g., systemic lupus erythematosus).

In some embodiments, the hemolytic disease or condition to be treated and/or prevented is the hemolytic disease or condition of a fetus of the pregnant mammal that is caused by an attack of the fetus' red blood cells by an antibody of the pregnant mammal. The combination or pharmaceutical composition can further comprise therapeutic agents for blocking and/or minimizing the attack of the fetus' red blood cells by an antibody of the pregnant mammal. For example, the additional therapeutic agents can be used to block and/or minimize the attack of the fetus' red blood cells by an antibody of the pregnant mammal, e.g., an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof.

In some embodiments, the hemolytic disease or condition to be treated and/or prevented is a hereditary hemolytic disease or disorder. The combination or pharmaceutical composition can further comprise therapeutic agents for treating and/or managing the hereditary hemolytic disease or disorder. For example, if hereditary hemolytic disease or disorder is glucose-6-phosphate dehydrogenase deficiency, the combination or pharmaceutical composition can further comprise folic acid. In another example, if hereditary hemolytic disease or disorder is sickle cell disease, the combination or pharmaceutical composition can further comprise folic acid, penicillin, anti-malarial chemoprophylaxis, an analgesic, opioid, nonsteroidal anti-inflammatory drugs (NSAID), an antibiotics, e.g., quinolone or macrolide, and/or hydroxyurea.

The combination or pharmaceutical composition can be administered using any suitable delivery mechanisms or techniques. In some embodiments, the combination or pharmaceutical composition can be administered via a medicament delivery system.

The combination or pharmaceutical composition can be administered via any suitable administration routes. In some embodiments, The combination or pharmaceutical composition can be administered via oral, parenteral, rectal, nasal, topical, or ocular routes, or by inhalation. Exemplary parenteral administration routes include intravenous, intramuscular, intraperitoneal, intranasal, and subcutaneous routes.

E. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000

µg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

One of ordinary skill in the art may modify the formulations within the teachings of the specification to provide numerous formulations for a particular route of administration. In particular, the nanoparticles, alone or in combination with other active ingredient(s), may be modified to render them more soluble in water or other vehicle. It is also well within the ordinary skill of the art to modify the route of administration and dosage regimen of a particular nanoparticle, alone or in combination with other active ingredient(s), in order to manage the pharmacokinetics of the present compounds for maximum beneficial effect in a patient.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for reducing antibody attack in a mammal, which method comprises administering, to a mammal in need of the reduction, an effective amount of a nanoparticle comprising a) an inner core comprising a material selected from the group consisting of poly(lactic-co-glycolic acid) (PLGA), polylactic acid (PLA), polyglycolic acid (PGA), polycaprolactone (PCL), polylysine, and polyglutamic acid, and b) an outer surface comprising a plasma membrane derived from a red blood cell, wherein:

said mammal is a pregnant mammal and said pregnant mammal's antibody attacks her fetus' red blood cells, or said mammal is a baby and said baby's red blood cells are attacked by an antibody of said baby's mother, and said pregnant mammal's antibody or said mother's antibody is an anti-A, anti-B, anti-rhesus D, anti-rhesus E, anti-rhesus c, anti-rhesus e, anti-rhesus C, anti-Kell, anti-Lewis, anti-Duffy, anti-Kidd, anti-P, anti-MN, or combinations thereof.

2. The method of claim 1, wherein the mammal is a human.

3. The method of claim 1, wherein the mammal is a pregnant mammal and the pregnant mammal's antibody attacks her fetus' red blood cells.

4. The method of claim 1, wherein the inner core supports the outer surface.

5. The method of claim 1, wherein the nanoparticle further comprises a releasable cargo.

6. The method of claim 1, wherein the nanoparticle substantially maintains natural structural integrity or activity of the cellular membrane or the constituents of the cellular membrane.

7. The method of claim 1, wherein the nanoparticle is biocompatible or biodegradable.

8. The method of claim 1, wherein the inner core of the nanoparticle comprises PLGA.

9. The method of claim 1, wherein the outer surface of the nanoparticle further comprises a synthetic membrane.

10. The method of claim 1, wherein the nanoparticle substantially lacks immunogenicity to the mammal.

11. The method of claim 1, which further comprises administering another active ingredient to the mammal.

12. The method of claim 1, which further comprises administering a pharmaceutically acceptable carrier or excipient to the mammal.

13. The method of claim 1, wherein the nanoparticle is administered via a medicament delivery system.

14. The method of claim 1, which further comprises assessing efficacy of nanoparticle and/or the another active ingredient in reducing antibody attack in the mammal.

15. The method of claim 1, wherein the nanoparticle, alone or in combination with other active ingredient(s), is administered via oral, parenteral, rectal, nasal, topical, or ocular routes, or by inhalation.

16. The method of claim 1, wherein the mammal is a baby and the baby's red blood cells are attacked by an antibody of the baby's mother.

* * * * *